US008624971B2

(12) United States Patent
Brown et al.

(10) Patent No.: US 8,624,971 B2
(45) Date of Patent: Jan. 7, 2014

(54) TDI SENSOR MODULES WITH LOCALIZED DRIVING AND SIGNAL PROCESSING CIRCUITRY FOR HIGH SPEED INSPECTION

(75) Inventors: David L. Brown, Sunnyvale, CA (US); Yung-Ho Chuang, Cupertino, CA (US)

(73) Assignee: KLA-Tencor Corporation, Milpitas, CA (US)

(*) Notice: Subject to any disclaimer, the term of this patent is extended or adjusted under 35 U.S.C. 154(b) by 1126 days.

(21) Appl. No.: 12/575,376

(22) Filed: Oct. 7, 2009

(65) Prior Publication Data

US 2010/0188655 A1 Jul. 29, 2010

Related U.S. Application Data

(60) Provisional application No. 61/146,652, filed on Jan. 23, 2009.

(51) Int. Cl.
*H04N 7/18* (2006.01)

(52) U.S. Cl.
USPC ............. 348/126; 348/87; 382/144; 382/145

(58) Field of Classification Search
USPC .............................. 348/87, 126; 382/144–145
See application file for complete search history.

(56) References Cited

U.S. PATENT DOCUMENTS

| | | | |
|---|---|---|---|
| 4,106,046 A | 8/1978 | Nathanson et al. | |
| 4,280,141 A | 7/1981 | McCann et al. | |
| 4,382,267 A | 5/1983 | Angle | |
| 4,580,155 A | 4/1986 | Tsoi et al. | |
| 5,440,648 A * | 8/1995 | Roberts et al. | 382/141 |
| 5,812,190 A * | 9/1998 | Audier et al. | 348/295 |
| 6,456,318 B1 | 9/2002 | Noguchi | |
| 7,046,283 B1 * | 5/2006 | Kamasz et al. | 348/295 |
| 7,227,984 B2 | 6/2007 | Cavan | |
| 7,233,350 B2 * | 6/2007 | Tay | 348/231.99 |
| 2001/0012069 A1 | 8/2001 | Derndinger et al. | |
| 2004/0175028 A1* | 9/2004 | Cavan | 382/145 |
| 2004/0212708 A1 | 10/2004 | Spartiotis et al. | |
| 2006/0087649 A1* | 4/2006 | Ogawa et al. | 356/237.5 |
| 2006/0103725 A1 | 5/2006 | Brown et al. | |
| 2007/0007429 A1 | 1/2007 | Fairley et al. | |
| 2007/0146693 A1 | 6/2007 | Brown et al. | |
| 2008/0002037 A1* | 1/2008 | Ueda | 348/223.1 |
| 2008/0079830 A1* | 4/2008 | Lepage | 348/295 |
| 2008/0232674 A1* | 9/2008 | Sakai et al. | 382/149 |
| 2008/0278775 A1* | 11/2008 | Katzir et al. | 358/482 |
| 2009/0079973 A1* | 3/2009 | Uto et al. | 356/237.2 |

FOREIGN PATENT DOCUMENTS

| | | | |
|---|---|---|---|
| EP | 0543629 A1 | 5/1993 | |
| EP | 2088763 A2 | 8/2009 | |
| KR | 1020020084541 A | 11/2002 | |

* cited by examiner

*Primary Examiner* — Duyen Doan
(74) *Attorney, Agent, or Firm* — Bever, Hoffman & Harms, LLP; Jeanette S. Harms

(57) ABSTRACT

An inspection system for inspecting a surface of a wafer/mask/reticle can include a modular array. The modular array can include a plurality of time delay integration (TDI) sensor modules, each TDI sensor module having a TDI sensor and a plurality of localized circuits for driving and processing the TDI sensor. At least one of the localized circuits can control a clock associated with the TDI sensor. At least one light pipe can be used to distribute a source illumination to the plurality of TDI sensor modules. The plurality of TDI sensor modules can be positioned capture a same inspection region or different inspection regions. The plurality of TDI sensor modules can be identical or provide for different integration stages. Spacing of the modules can be arranged to provide 100% coverage of the inspection region in one pass or for fractional coverage requiring two or more passes for complete coverage.

46 Claims, 14 Drawing Sheets

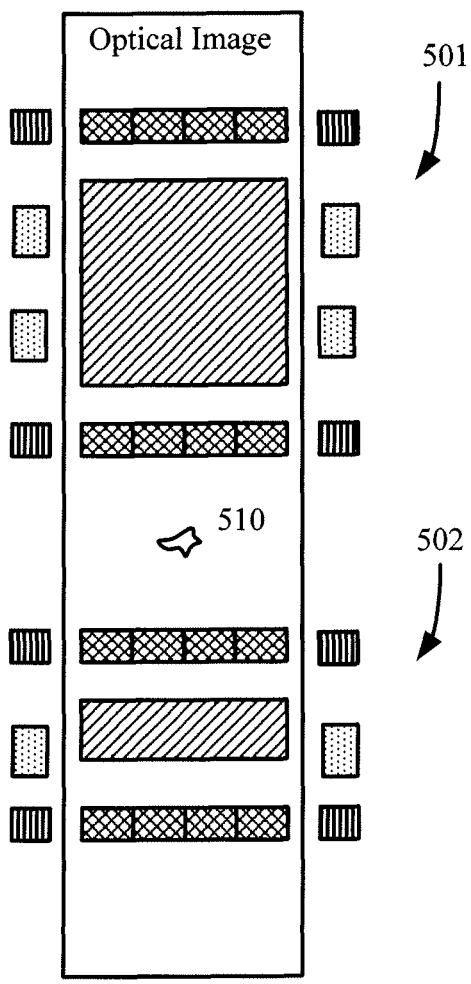
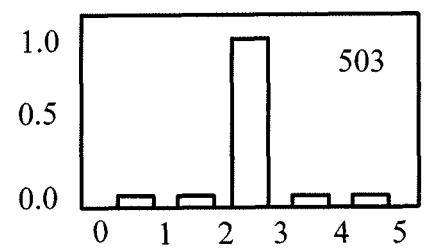
FIG. 5B
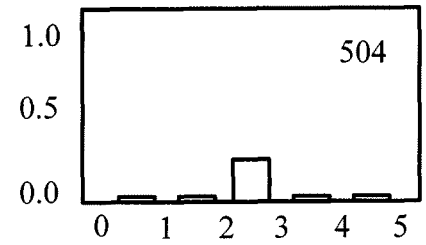
FIG. 5C
FIG. 5A

US 8,624,971 B2

TDI SENSOR MODULES WITH LOCALIZED DRIVING AND SIGNAL PROCESSING CIRCUITRY FOR HIGH SPEED INSPECTION

RELATED APPLICATIONS

This application claims priority of U.S. Provisional Patent Application 61/146,652, entitled "High-Dynamic-Range Illumination And Multi-Sensor Architecture For Inspection Systems" filed Jan. 23, 2009.

BACKGROUND OF THE INVENTION

1. Field of the Invention

The present invention relates to an inspection system for wafers, masks, and/or reticles. The inspection system can include an array of TDI sensor modules with localized circuitry for driving and signal processing.

2. Related Art

Time delay integration (TDI) is an imaging process that produces a continuous image of a moving two-dimensional object. In a TDI system, image photons are converted to photocharges in an array of pixels. As the object is moved, the photocharges are shifted from pixel to pixel down the sensor, parallel to the axis of movement. By synchronizing the photocharge shift rate with the velocity of the object, the TDI can integrate a signal intensity at a fixed position on the moving object to generate the image. The total integration time can be regulated by changing the speed of the image motion and providing more/less pixels in the direction of the movement. TDI inspection systems can be used for inspecting wafers, masks, and/or reticles.

A conventional TDI sensor includes a large array of photo sensor elements (e.g. charge-coupled devices (CCDs)) formed as a grid. For example, a conventional TDI sensor could be formed in a 2048×256 array of photo sensor elements. Exemplary, conventional TDI sensors are described in U.S. Pat. No. 4,580,155, which issued to Tsoi et al. on Apr. 1, 1986, U.S. Pat. No. 4,280,141, which issued to McCann on Jul. 21, 1981, and U.S. Pat. No. 4,382,267, which issued to Angle on May 3, 1983.

To achieve higher sensitivity than can be provided by using a conventional TDI sensor, U.S. Pat. No. 7,227,984, which issued to Cavan on Jun. 5, 2007, arranges a plurality of TDI pixels in a sub-pixel offset pattern. FIG. 1 illustrates a simplified, interleaved TDI sensor 100 including two sensor arrays 101 and 102 that are formed in an interleaved pattern. This sensor interleaving can advantageously increase the resolution and the anti-aliasing capability of a TDI inspection system. Each sensor array includes a plurality of hexagon-shaped pixels 103, wherein each sensor array is offset both in the vertical direction and the horizontal direction relative to an adjacent sensor array. Note that each offset is a sub-pixel distance, i.e. less than one pixel.

At increasingly smaller technology nodes, it is desirable for the image to be significantly magnified, thereby facilitating defect detection. At the same time, faster inspections are being requested, despite the increasing complexity of the wafers/masks/reticles being inspected. To accomplish these goals, the size of the TDI sensor arrays has increased.

Unfortunately, the yield associated with TDI sensor arrays decreases significantly with increases in array size. Moreover, larger TDI sensor arrays also have correspondingly larger drivers, which require more current. Additionally, the analog readout from these large sensor arrays requires dense signal trace routing and large complicated printed circuit boards. The dense signal routing increases the possibility of signal crosstalk, which can decrease the signal-to-noise ratio (SNR). Moreover, high-brightness illumination is required to provide an intense, uniform field of illumination at the inspection surface plane. The decreased yield as well as the increased driving, processing, and illumination requirements can significantly increase system resource and component costs.

Therefore, a need arises for a TDI-based inspection system that employs smaller TDI devices while mitigating the driving, processing, and illumination difficulties.

SUMMARY OF THE INVENTION

An inspection system for inspecting a surface of a wafer/mask/reticle is described. This inspection system can include a modular array, an optical system, and an image processor. The modular array can include a plurality of time delay integration (TDI) sensor modules. Each TDI sensor module can include a TDI sensor and a plurality of localized circuits for driving and processing the TDI sensor. At least one of the localized circuits can control a clock associated with the TDI sensor. The optical system can be configured to receive light from the surface and direct portions of the light onto the plurality of TDI sensor modules. The image processor can be configured for receiving data from the modular array.

In one embodiment, the modular array can further include a printed circuit board (PCB) for mounting and coupling the TDI sensor and the plurality of localized circuits. A data transceiver can be mounted on the PCB on an opposite side from the TDI sensor and the plurality of localized circuits. In this configuration, at least one processing circuit of the plurality of localized circuits can be coupled to the data transceiver.

In one embodiment, at least one of the localized circuits is a field programmable gate array (FPGA), e.g. mounted on the PCB. This FPGA can receive digitized signals from at least one other of the plurality of localized circuits. In one embodiment, the plurality of localized circuits and the FPGA can be mounted on the PCB on the opposite side from the TDI sensor (and the same side as the transceiver).

In another embodiment, a silicon substrate can be used instead of the PCB. Advantageously, because the silicon substrate, the TDI sensor, and the localized circuits have substantially the same thermal coefficient of expansion, an inspection system including this modular array can efficiently diffuse heat generated in the TDI sensor with low thermally-induced mechanical stress and high reliability.

The inspection system can further include at least one light pipe to distribute a low-brightness source illumination to the plurality of TDI sensor modules. In one embodiment, a plurality of light pipes can be used to equally distribute the source illumination to the plurality of TDI sensor modules. In another embodiment, the inspection system can further include a prism to segment and distribute light from the light pipe(s) to the plurality of TDI sensor modules. In yet another embodiment, the inspection system can further include mirrors to segment and distribute light from the light pipe(s) to the plurality of TDI sensor modules.

In one embodiment, a first row of TDI sensor modules is offset (i.e. lateral to a TDI scan direction or in the TDI scan direction) with respect to a second row of TDI sensor modules. In another embodiment, the plurality of TDI sensor modules can be aligned in a TDI scan direction.

In one embodiment, the plurality of TDI sensor modules can capture a same inspection region. In another embodiment, a first set of the plurality of TDI sensor modules can be aligned in a TDI scan direction, a second set of the plurality of TDI sensor modules can be aligned in the TDI scan direction, and the first and second sets of TDI sensor modules can capture different inspection regions.

The plurality of TDI sensor modules can be identical or not identical. For example, in one embodiment, the plurality of TDI sensor modules can include at least two TDI sensors having different integration stages.

A method of forming a modular array for an inspection system is also described. In this method, a plurality of time delay integration (TDI) sensors can be formed. A plurality of circuits for driving and processing data from the plurality of TDI sensors can also be formed. Notably, each TDI sensor has a unique set of the plurality of circuits locally positioned near the TDI sensor.

As described below in further detail, a modular array including a plurality of TDI sensor modules can facilitate scaling, compensate for saturation, improve dynamic range, reduce aliasing, account for pixel alignment, provide data manipulation, identify the occurrence of radioactive events/ cosmic rays, increase effective data rates, improve signal-to-noise ratios, and ensure a robust inspection system.

BRIEF DESCRIPTION OF THE FIGURES

FIG. 5A illustrates an exemplary configuration for a modular array in which TDI sensor modules providing redundant data can have different sensitivities.

FIGS. 5B and 5C illustrate exemplary defect signal plots using the configuration shown in FIG. 5A.

DETAILED DESCRIPTION OF THE FIGURES

In accordance with an improved inspection system, a TDI sensor module can advantageously include localized circuitry for driving and signal processing. A module array including these TDI sensor modules can increase yield while decreasing driving and processing requirements. The improved inspection system can further include one or more light pipes that equally distribute light from a low-brightness source onto the modular array, thereby reducing illumination requirements compared to conventional TDI sensors.

Figure 1:
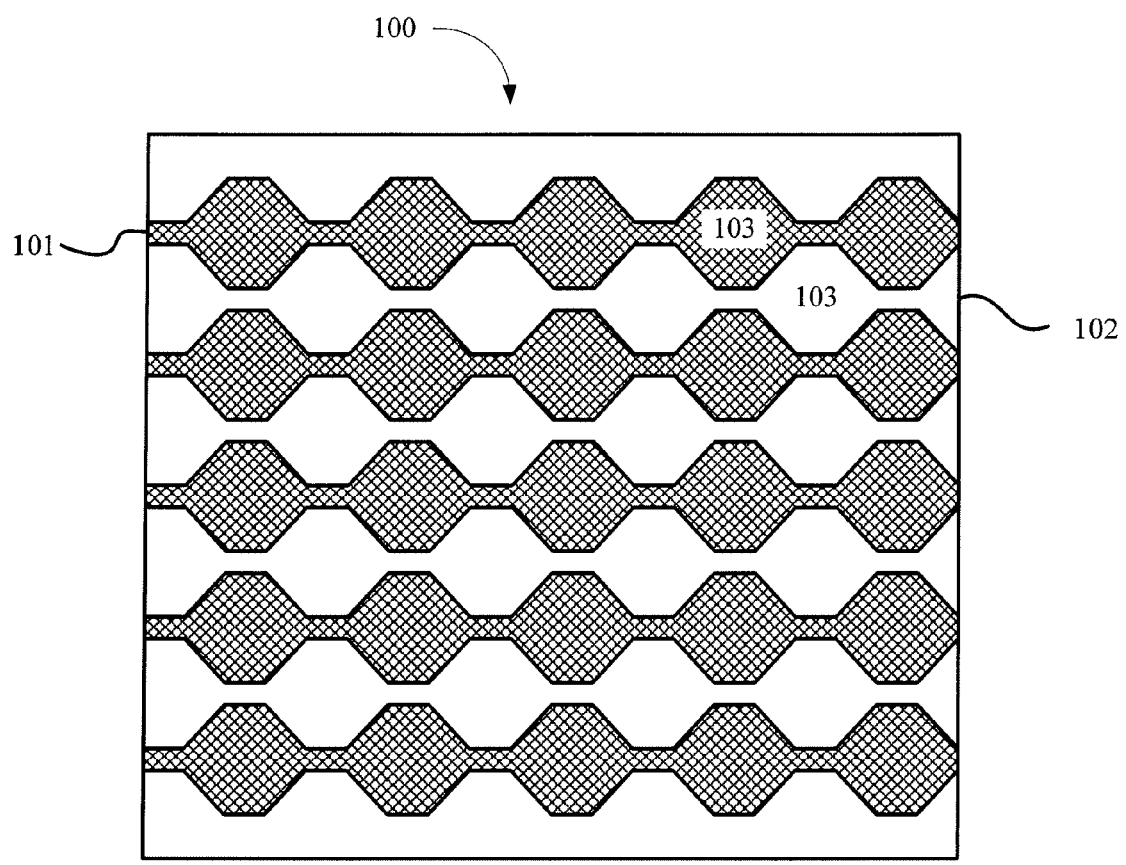
FIG. 1 illustrates a TDI sensor array including interleaved TDI sensors.
Figure 2A:
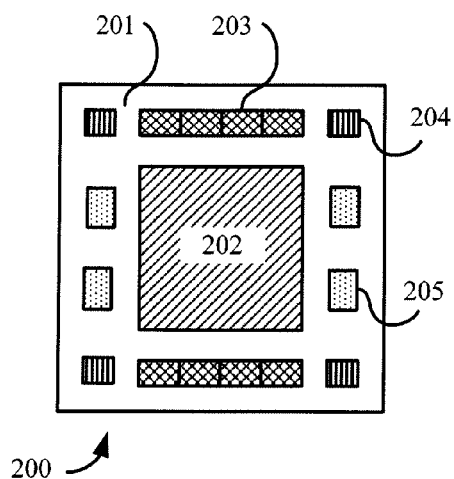
FIG. 2A illustrates an exemplary TDI sensor module including localized driving and signal processing circuitry.

FIG. 2A illustrates a top view of an exemplary TDI sensor module 200 that includes localized driving and signal processing circuitry (also called localized circuits herein). Specifically, TDI sensor module 200 includes a TDI sensor 202, processing circuits 203 for processing the signals from TDI sensor 202, timing and serial drive circuits 204, and pixel gate driver circuits 205.

In one embodiment, processing circuits 203 can provide correlated double sampling (CDS) and other analog front end (AFE) functions (e.g. analog gain control), analog to digital conversion (ADC), and digital post-processing such as black-level correction, per pixel gain and offset corrections, linearity corrections, look-up tables (LUTs), and data compression. The processing may be fixed or rely on additional, possibly real-time, input from the inspection system to perform functions such as sub-pixel interpolation, analog gain control to prevent digital saturation, image position shifting, and image spatial distortion correction. In one embodiment, processing circuits 203 can manipulate various captured images in the analog or digital domain (described in further detail below), thereby saving communication and processing bandwidth in an image analysis computer of the inspection system.

The timing and serial drive circuits 204 can control clock timing and drive for TDI. Features such as reset pulse generation, multi-phase serial-register clock generation, and ADC synchronization may be included. This allows for very accurate timing which is needed to achieve high SNR at high clocking speeds.

The pixel gate driver circuits 205 provide slower but higher-current TDI gate drive signals to synchronize data capture with the inspection image motion and with other TDI sensors. Pixel gate driver circuits 205 may typically provide three-phase or four-phase drive waveforms of square-wave and/or sinusoidal waveforms. More generally, pixel gate driver circuits 205 may use digital-to-analog conversion to provide arbitrary function generation in order to optimize the charge transfer, thermal dissipation, and SNR of the sensor. U.S. patent application Ser. No. 10/992,063, entitled "Continuous Clocking Of TDI Sensors", which is incorporated by reference herein, describes this digital-to-analog conversion in greater detail.

Advantageously, localized driving circuits mean that each TDI sensor module has its own individual set of drivers (i.e. drivers 204 and 205). These individual drivers require significantly less current, and thus can be significantly smaller than conventional large-area TDI sensor drivers. Notably, locally distributing high fidelity, high-current waveforms from a plurality of small drivers (associated with the TDI sensor modules) is much more scalable than distributing waveforms from one large driver, even when the total current requirement is the same.

Figure 2B:
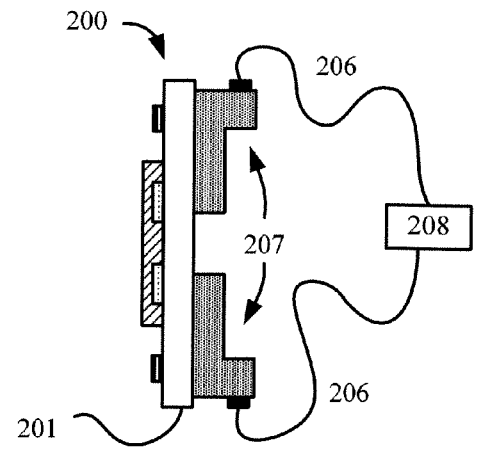
FIG. 2B illustrates a side view of the TDI sensor module of FIG. 2A.

In one embodiment, each of processing circuits 203, timing and serial drive circuits 204, and pixel gate drive circuits 205 can be implemented on integrated circuits positioned around TDI sensor 202 on a PCB (printed circuit board) 201. Note that the number of ICs used to implement the driving/processing circuits can vary based on embodiment. In one embodiment, PCB 201 can be implemented using a multi-layer, ceramic substrate. FIG. 2B illustrates a side view of an exemplary PCB 201 including data transceivers 207 (e.g. 10 Gigabit optical transceivers) connected to PCB 201, wherein PCB 201 includes wiring (not shown for simplicity) in communication with the driving/processing circuits of TDI sensor module 200. In one embodiment, optical fibers 206 can be attached to data transceivers 207 to allow communication of driving/processing data between TDI sensor module 200 and system-level inspection components 208. In one embodiment, digital data from TDI sensor module 200 can be transmitted off-board using low voltage differential signaling (LVDS), or similar electrical signaling and digital multiplexing. The specific protocol can be selected from an industry standard or prescribed by those skilled in the art of electronic or optical high-speed digital communications.

Figure 3:
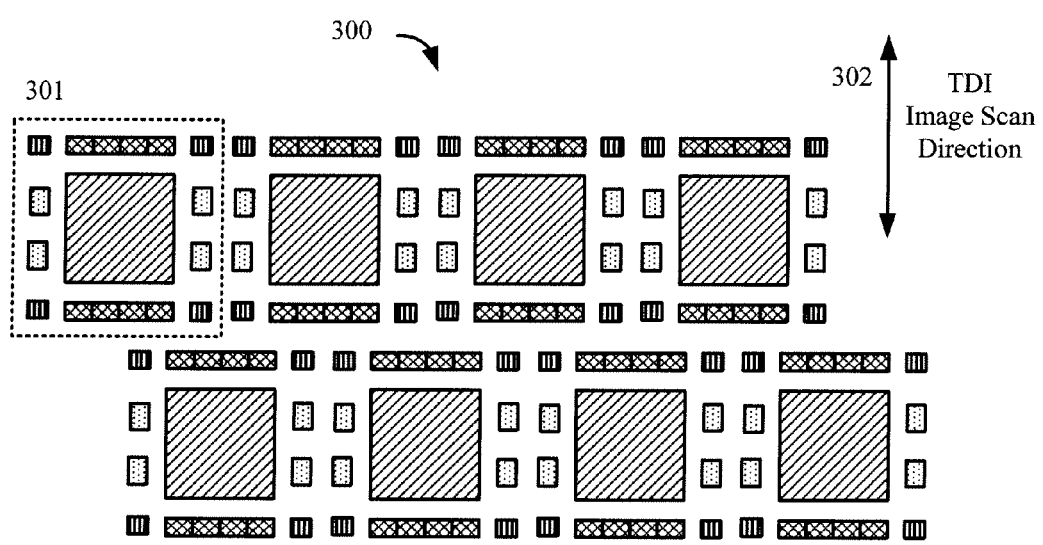
FIG. 3 illustrates an exemplary modular array including a plurality of TDI sensor modules positioned in two offset rows.

FIG. 3 illustrates an exemplary modular array 300 of TDI sensor modules 301 (hereinafter called a modular sensor array). Note that the driving/processing circuits positioned around the TDI sensor take up a predetermined space. Thus, the TDI sensors in adjacent rows can be aligned such that at least 100% image coverage is achieved when used in a continuous scanning configuration. For example, in the embodiment shown in FIG. 3, each row can be offset with respect to an adjacent row such that the TDI sensor is positioned in the same vertical space as the driving/processing circuits of an adjacent row. To ensure no gaps in image coverage, the width of each TDI sensor is equal to or greater than the space between TDI sensors. In this configuration, as the inspected wafer/mask/reticle is being moved in a TDI image scan direction 302, modular sensor array 300 can ensure at least 100% image capture.

In one embodiment, some minimal overlap between TDI sensors from adjacent rows can provide redundant data. This redundant data can, for example, confirm accurate alignment of the images generated by TDI sensor modules 301. In one embodiment of minimal overlap, the inspection system can arbitrarily select the data from one TDI sensor module to be used for the edge pixels. In another embodiment, the inspection system can combine data from multiple TDI sensor modules to achieve higher quality data near edge pixels.

Note that the effective data rate for modular array 300 can be significantly higher than a single, large TDI sensor. This rate is achieved because the modular array can have an effective total size and number of output channels that is larger than can be be practically manufactured in a single TDI sensor.

Figure 4:
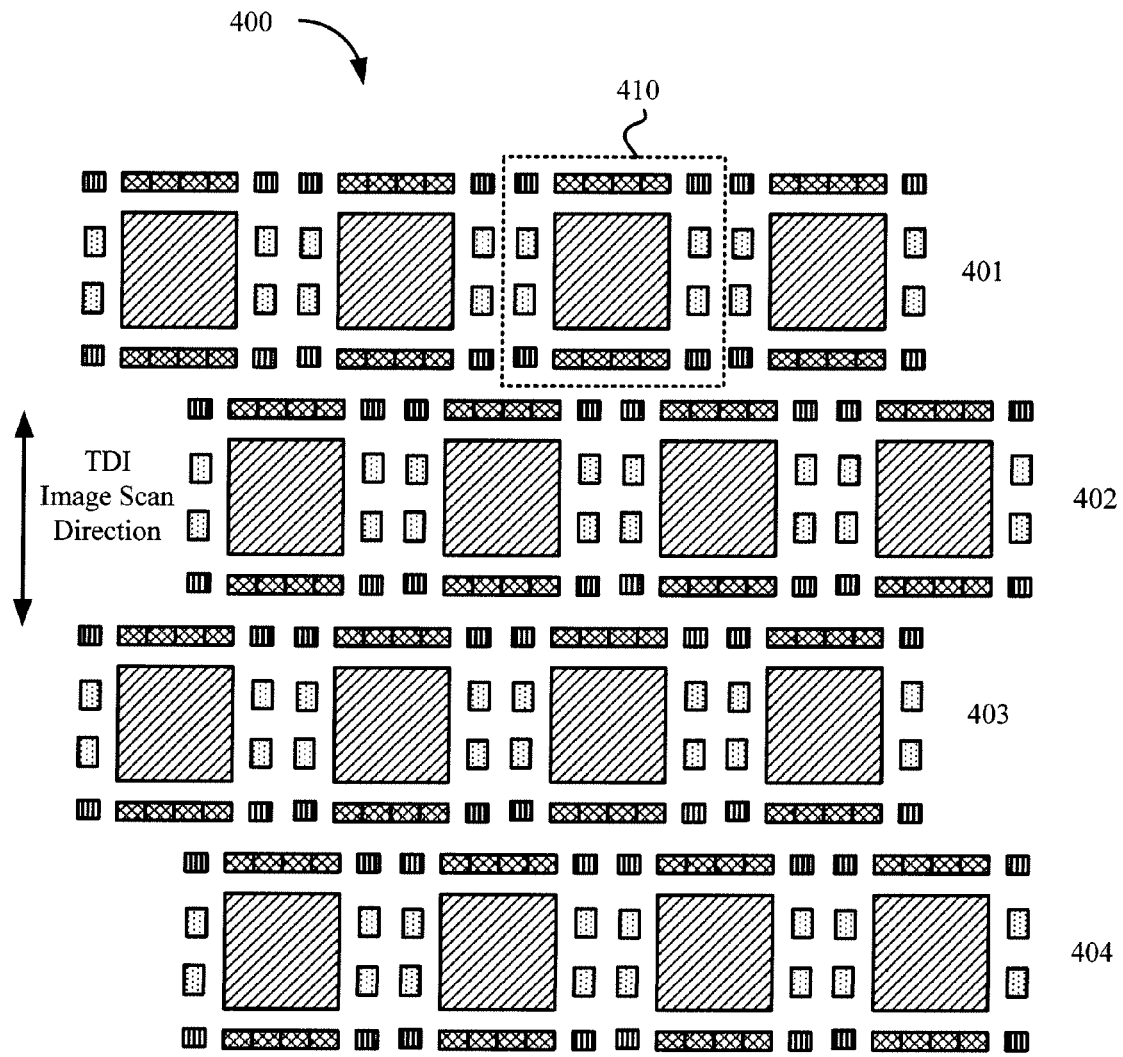
FIG. 4 illustrates an exemplary modular array including a plurality of TDI sensor modules positioned in four offset rows to provide redundant data.

Further note that any number of rows of TDI sensor modules can be included in a modular array, i.e. TDI sensor modules facilitate scaling. This scaling yields additional information. For example, FIG. 4 illustrates an exemplary modular array 400 including four rows 401, 402, 403, and 404 of TDI sensor modules 410. In this embodiment, rows 401 and 403 capture and process independent samples of the same (or very similar) optical image data. Similarly, rows 402 and 404 capture and process substantially similar data. Thus, modular array 400 can advantageously provide two independent data streams for each swath of the inspected wafer/mask/reticle. The additional data can provide significant advantages during wafer inspection.

For example, one inspection problem that can be successfully addressed by a modular array is saturation. Specifically, DUV (deep ultraviolet) and EUV (extreme ultraviolet) light sources are quite dim. Therefore, TDI sensors are typically designed for high sensitivity. However, when a large, bright defect is present, a high sensitivity TDI sensor may saturate. Under those conditions, an inspection system cannot accurately determine the size or other details of the defect.

FIG. 5A illustrates an exemplary configuration that can be used to improve dynamic range. Specifically, high sensitivity TDI sensor module 501 and a low sensitivity TDI sensor module 502 are positioned to capture and process substantially similar image data (additional TDI sensor modules in their respective rows are not shown for simplicity). Notably, TDI sensor module 502 can include a narrow TDI sensor that integrates at most a few lines (or even a sensor that integrates only one line), where TDI sensor module 501 can include a wide TDI sensor that integrates hundreds or even thousands of times (based on the number of pixels in the direction of the TDI image scan). In this configuration, even if the TDI sensor of TDI sensor module 501 saturates (as shown in defect signal plot 503 of FIG. 5B) because of a bright defect 510, the sensor of TDI sensor module 501 probably will not saturate (as shown in defect signal plot 504 of FIG. 5C). Therefore, a modular array comprising rows of TDI sensor modules 501 and 502 can advantageously increase the dynamic range of an inspection system. Note that when the TDI sensors are positioned in the same vertical position (as opposed to offset, as shown in FIG. 4), after one TDI (e.g. vertical) scan is complete, the object to be inspected can be shifted horizontally and then scanned in the opposite vertical direction, thereby achieving the same result as having offset rows of TDI sensors.

Figure 6B:
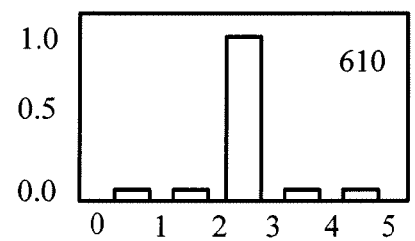
FIGS. 6B and 6C illustrate exemplary defect signal plots using the configuration shown in FIG. 6A.
Figure 6A:
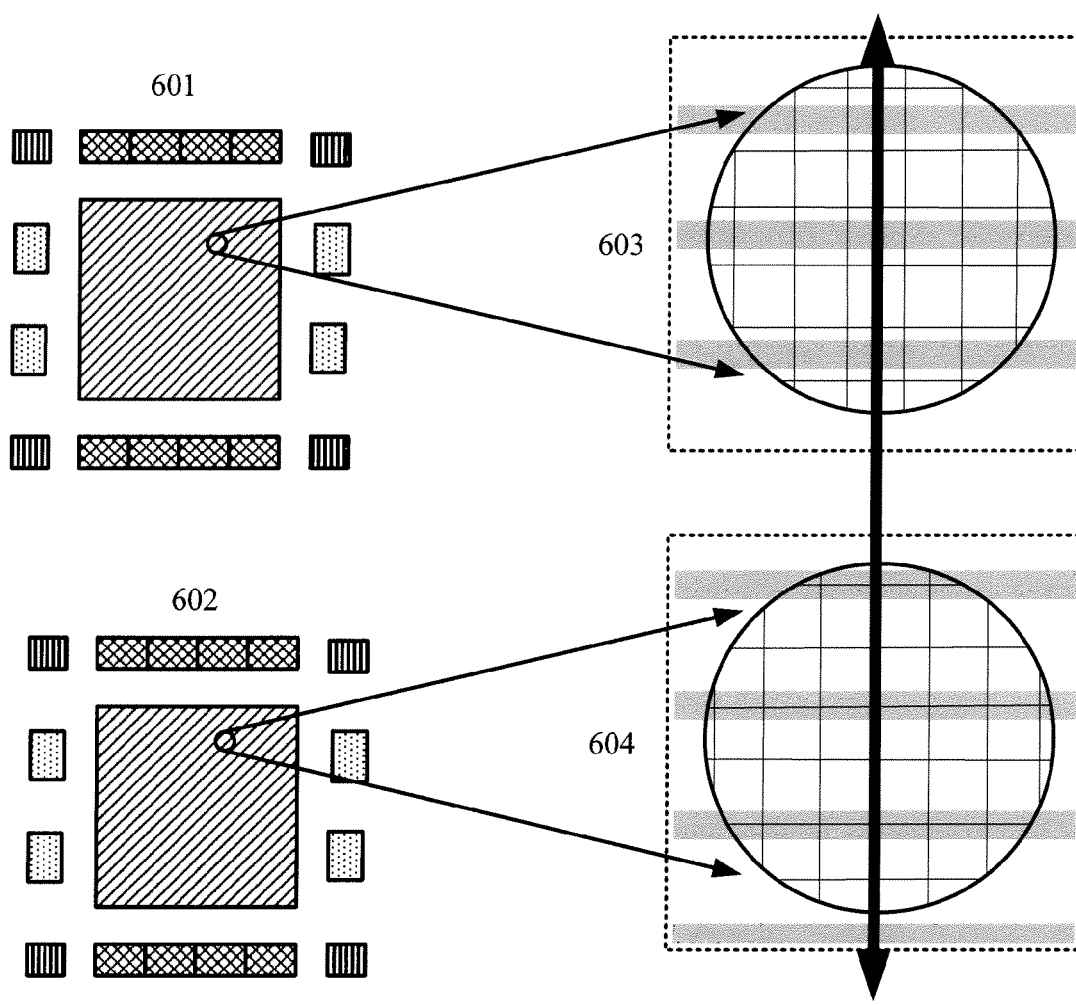
FIG. 6A illustrates an exemplary configuration for a modular array in which TDI sensor modules providing redundant data can have a slight lateral offset with respect to each other.

Another inspection problem that can be successfully addressed by a modular array is aliasing due to pixel alignment. FIG. 6A illustrates a modular array including TDI sensor modules 601 and 602 (the TDI sensor modules in their respective rows are not shown for simplicity). In this embodiment, TDI sensor module 602 is slightly offset horizontally, e.g. on the order of 0.5 pixel, from TDI sensor module 601 (wherein TDI sensor modules in their respective rows could be similarly offset)(i.e. a lateral relative pixel shift). This offset is more clearly shown in magnified spots 603 and 604. Note that TDI sensor module 601 pixels are aligned with an image feature (shown as a grid pattern and line in magnified spot 603), whereas TDI sensor module 601 pixels are not aligned with the image feature (as shown in magnified spot 604). Note that the vertical alignment can be n pixels, where n is an integer and where the physical separation is n times the pixel spacing. The separation n may be a large number in this embodiment. For example, if m is the TDI number of integration stages (pixels in vertical direction) then n may conveniently be set to 2 m, 2 m+1, or similar spacing that allows for placement of drivers and other components.

A potential defect can be detected by comparing a signal magnitude to a predetermined threshold, which is set higher than the noise level of the signal. For example, in one embodiment, a normalized threshold of 0.5 could be used. Conventional TDI sensor arrays can detect a feature aligned with the pixels or not, but not both cases at once. Therefore, should the TDI sensor have the alignment relative to a feature shown in magnified spot 603, a conventional TDI sensor array could miss a defect that is straddling two pixels and therefore may have a signal for each pixel that is less than the predetermined threshold. To overcome this pixel alignment issue, a conventional technique sets the magnification such that a single optical resolution spot covers more than one pixel. Unfortunately, the greater magnification slows the inspection significantly.

Figure 6C:
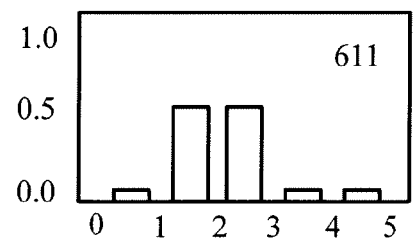

In contrast, by using a configuration for the module array shown in FIG. 6A, data from image features aligned with TDI sensor pixels (e.g. TDI sensor module 601) as well as from those not well aligned (e.g. TDI sensor module 602) can be captured. For example, defect signal plot 610 in FIG. 6B corresponds with data from TDI sensor module 601, whereas defect signal plot 611 in FIG. 6C corresponds with data from TDI sensor module 602. This additional data can be advantageously used to detect potential defects that would otherwise not be detected by conventional TDI sensor arrays. That is, by comparing defect signal plots 610 and 611, an inspection system can more easily determine that a potential defect exists (i.e. both defect signal plots 610 and 611 have signals at the same location taking into account pixel offset) and then follow this detection with additional processing to determine defect severity, for example. Thus, this technique can be characterized as reducing the negative effects of aliasing. Moreover, this configuration can provide potential defect detection without increasing magnification, thereby ensuring the fastest possible inspection.

Figure 7B:
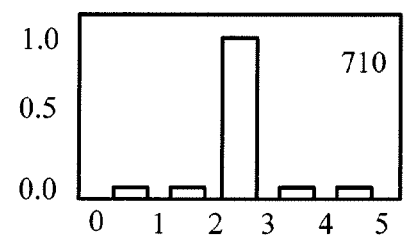
FIGS. 7B and 7C illustrate exemplary defect signal plots using the configuration shown in FIG. 7A.
Figure 7A:
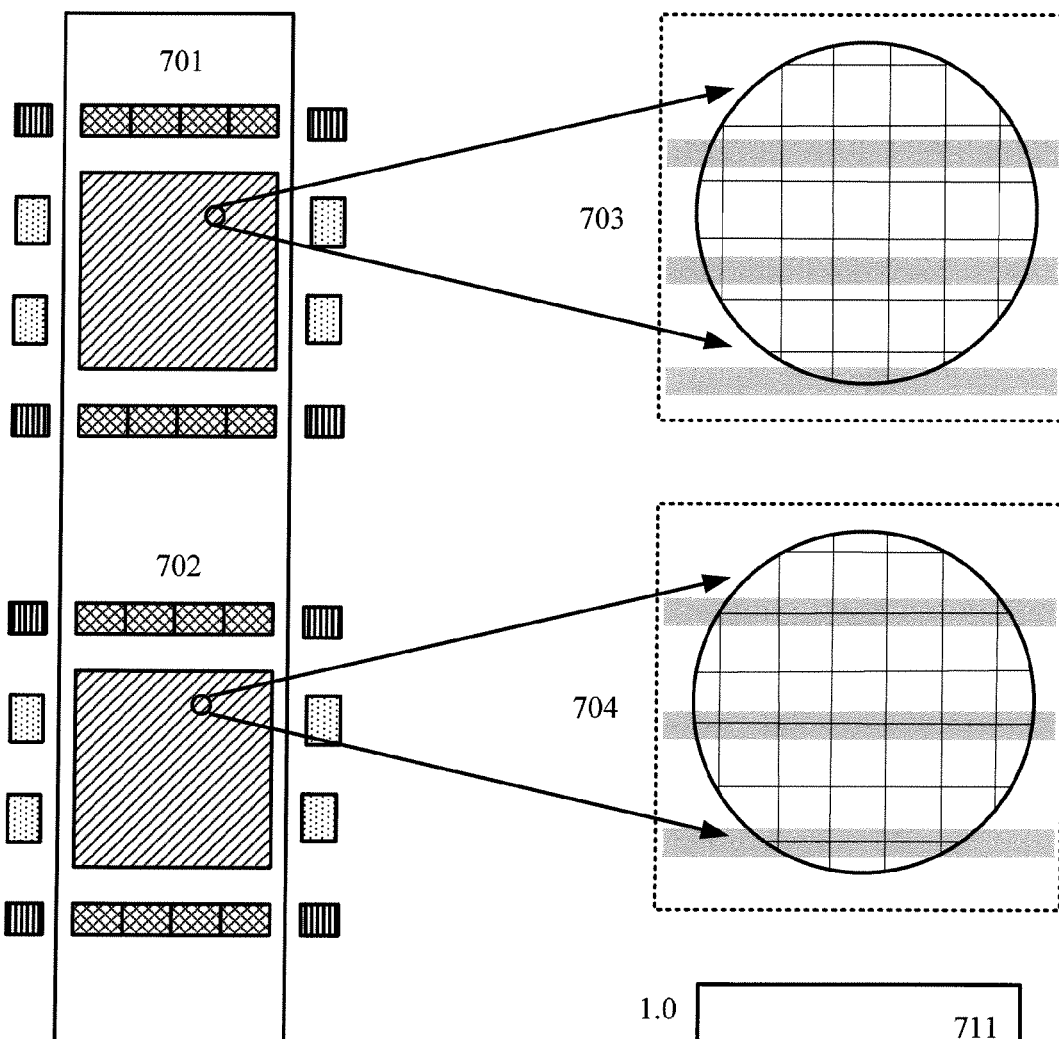
FIG. 7A illustrates an exemplary configuration for a modular array in which TDI sensor modules providing redundant data can have a slight offset in the scan direction with respect to each other.
Figure 7C:
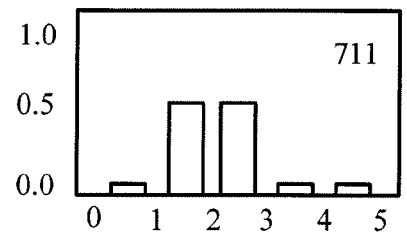

Note that offsetting the TDI sensor modules in the direction of the TDI scan can also provide additional information. For example, FIG. 7A illustrates a modular array including TDI sensor modules 701 and 702 (the TDI sensor modules in their respective rows are not shown for simplicity). In this embodiment, TDI sensor module 702 is slightly offset vertically, e.g. on the order of 0.5 pixel, from TDI sensor module 701 (wherein TDI sensor modules in their respective rows could be similarly offset)(i.e. a relative pixel shift in the scan direction). This offset is more clearly shown in magnified spots 703 and 704. Note that TDI sensor module 701 is aligned with the pixels (shown as a grid pattern in magnified spot 703), whereas TDI sensor module 701 is aligned between pixels (also called pixel border aligned)(as shown in magnified spot 704). Defect signal plot 710 in FIG. 7B corresponds with data from TDI sensor module 701, whereas defect signal plot 711 in FIG. 7C corresponds with data from TDI sensor module 702. In the case of two TDIs in series, the devices may be conveniently placed, for TDIs with m integration stages, at 2 m+0.5 pixels separation, 2 m+1.5, etc.

This configuration can also facilitate potential defect detection. That is, similar to the configuration shown in FIG. 7A, the slight offset of the TDI sensor modules, in this case in the vertical direction, can advantageously provide additional data that can aid in detecting potential defects. Note that although a physical offset can be used, because the offset is associated with the scan direction, an equivalent offset can be accomplished more easily by manipulating the clocking of the TDI imaging (e.g. shifting by +90 degrees, −90 degrees, etc). In addition, by specifying the relative timing of the TDI line clocks after the array assembly construction, the vertical spacing mechanical tolerances can be loosened.

Figure 8B:
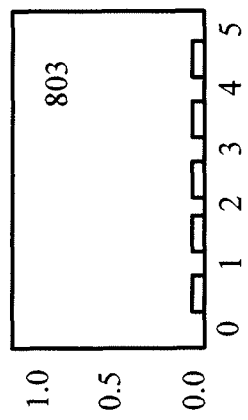
FIGS. 8B and 8C illustrate exemplary defect signal plots using the configuration shown in FIG. 8A.
Figure 8C:
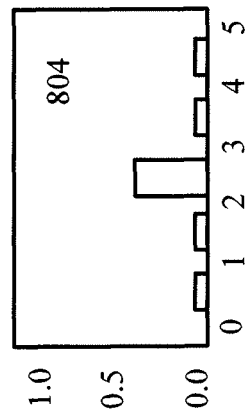
Figure 8D:
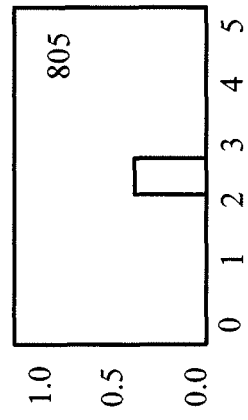
FIG. 8D illustrates a derived defect signal plot using the defect signal plots of FIGS. 8B and 8C.
Figure 8A:
FIG. 8A illustrates an exemplary configuration for a modular array in which TDI sensor modules providing redundant data can have low sensitivities.
Figure 8A:
Figure 8A:
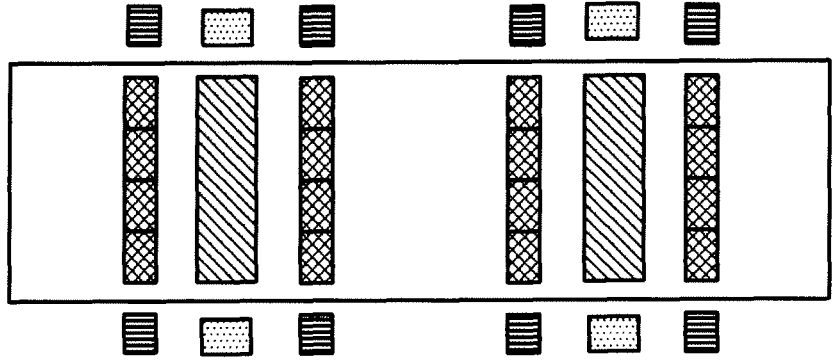

FIG. 8A illustrates two TDI sensor modules 801 and 802 (and their respective rows of TDI sensor modules) that can be used in combination with different filters. For example, in one embodiment, TDI sensor module 801 can be used with a visible light filter (for allowing wavelengths associated with visible light) to generate a defect signal plot 803 in FIG. 8B, whereas TDI sensor module 802 can be used with a UV filter (for allowing wavelengths associated with UV light) to generate a defect signal plot 804 in FIG. 8C.

In one embodiment, a simple mathematical operation (e.g. subtraction or addition) can be performed, after suitable preprocessing that might include calibration and image registration/alignment, using defect signal plots 803 and 804 to extract pertinent information. For example, FIG. 8D illustrates a defect signal plot 805 that results from defect signal plot 803 being subtracted from defect signal plot 804. Note that any number of filters can be used with any TDI sensor module set. For example, in one "color" filter embodiment, each filter could be associated with a specific optical wavelength spectrum, e.g. red, blue, and ultraviolet. In this case, the three resulting images could be summed to generate a "gray-scale" image. Simultaneously, the same data can be processed by subtracting, for example, the ultraviolet image channel from the blue image channel. In another embodiment, each TDI sensor module can be used with a different polarization filter, e.g. vertical, horizontal, or even circular polarizations.

Figure 9A:
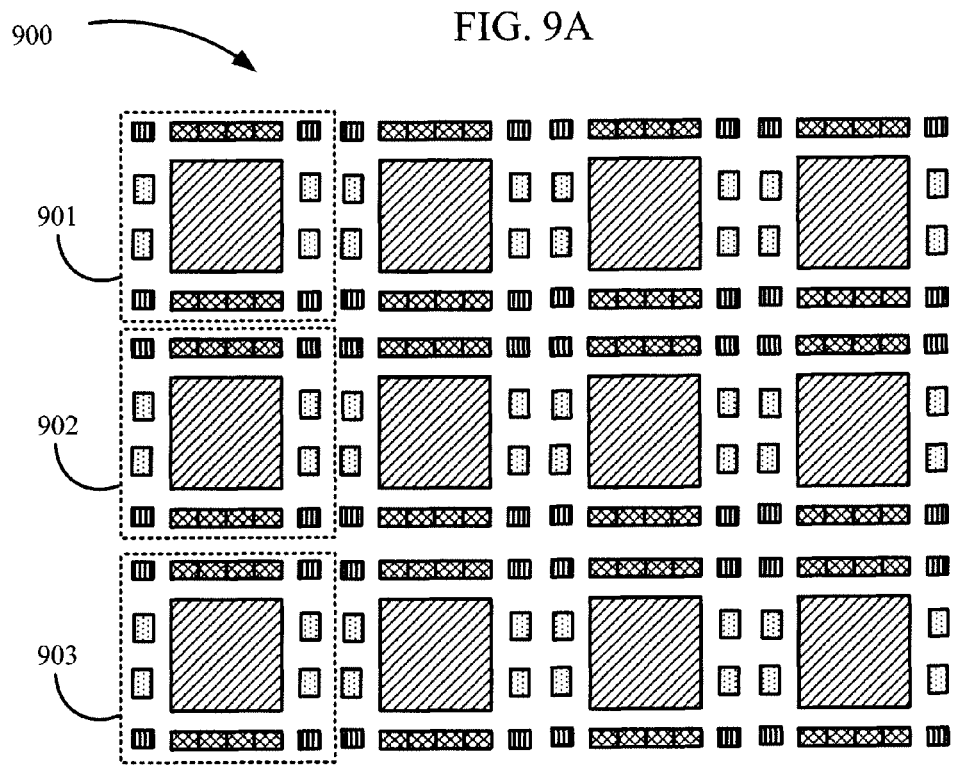
FIG. 9A illustrates an exemplary modular array in which TDI sensor modules can be positioned to distinguish between potential defects and the occurrence of a radioactive event or cosmic ray.
Figure 9B:
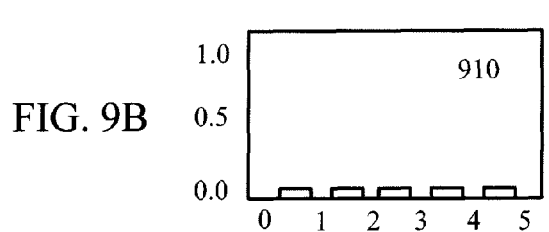
FIGS. 9B, 9C, 9D, and 9E illustrate exemplary defect signal plots for three TDI sensor modules in the modular array shown in FIG. 6A.
Figure 9C:
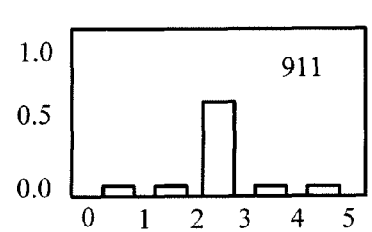
Figure 9D:
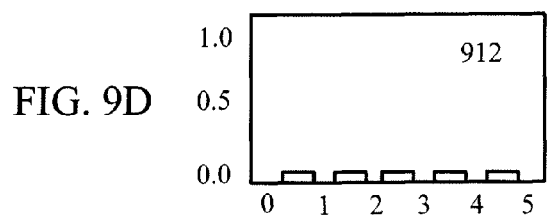
Figure 9E:
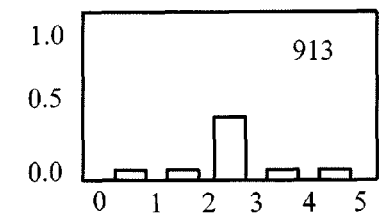

Another inspection problem that can be successfully addressed by a modular array is the occurrence of radioactive events or cosmic rays. Specifically, just as any TDI sensor is sensitive to light, it is also sensitive to both radioactive events and cosmic rays. The challenge during inspection is to distinguish between such occurrences (which are not part of the optical image, but still affect the TDI sensor data) and an actual defect on the wafer/mask/reticle. FIG. 9A illustrates one embodiment of a module array 900 that can distinguish between radioactive events/cosmic rays and actual defects. In this embodiment, TDI sensor modules 901, 902, and 903 are aligned in the scan direction. In this configuration, if TDI sensor module 902 registers a charge on the image (see defect signal plot 911 in FIG. 9C) but TDI sensor modules 901 and 903 do not register a charge at the same location on the image (see defect signal plots 910 and 912 in FIGS. 9B and 9D, respectively), then the inspection system may reject these results as an occurrence of a real physical defect. On the other hand, if TDI sensor module 902 registers a charge on the image (see defect signal plot 911 in FIG. 9C) and TDI sensor modules 901 and 903 register a similar charge magnitude at the same location on the image (see defect signal plot 913 in FIG. 9E), then the inspection system may interpret these results as an occurrence of a defect or a normal image feature by using conventional defect detection methods.

Note that back-illuminated TDI sensors are relatively thin devices, thereby allowing many radioactive particles and cosmic rays to easily pass through without producing a signal. However, if TDI sensors are made thicker to increase durability and yield, then the probability that the TDI sensors will detect such radioactive particles and cosmic rays increases. Moreover, an increase in TDI sensor thickness results in an exponential increase in the detection of some radioactive particles/cosmic rays. Advantageously, using array modules that provide redundant data (as shown in array module 900 and other embodiments herein), thereby allowing comparison of images from different TDI sensor modules, can efficiently identify the occurrence of radioactive events/cosmic rays.

As described above, a modular array including a plurality of TDI sensor modules can facilitate scaling, compensate for saturation, improve dynamic range, reduce aliasing, account for pixel alignment, provide data manipulation, identify the occurrence of radioactive events/cosmic rays, improve yield, and increase effective data rates.

Additionally, with additional information being available from multiple TDI sensors, if one TDI sensor degrades or is has a small defective region (either previously-known or determined during operation), then the inspection system can advantageously ignore data from that sensor or sensor region. Repairs can be made if and when desired by the operator. Therefore, a modular array including TDI sensor modules also ensures a robust inspection system and with reduced or more predictable maintenance schedule.

An additional advantage of using modular arrays is an increased signal-to-noise ratio (SNR). Note that for visible light, the energy of the photon is generally sufficient to excite one electron into a conduction state. That is, one photon typically results in not more than one signal-generating electron. However, as the energy of the photon becomes higher, additional electrons can enter into a conduction state and be collected. For example, at EUV (13 nm), the energy of one photon is sufficient to excite approximately 25 electrons into a conduction state. So, for a given TDI sensor electron well capacity per pixel, the photon detection level is effectively 25 times less for EUV light. Also, because photon shot noise is inversely proportional to the square root of the collected photons, the noise level will be higher for the EUV case compared to the visible light case.

The above-described modular array can advantageously improve the noise characteristics of the inspection system (i.e. the SNR). Specifically, having two TDI sensor modules collecting redundant image data can improve the SNR by a square root of 2 and, by extension, having N TDI sensor modules collecting redundant data can improve the SNR by a square root of N.

Figure 10:
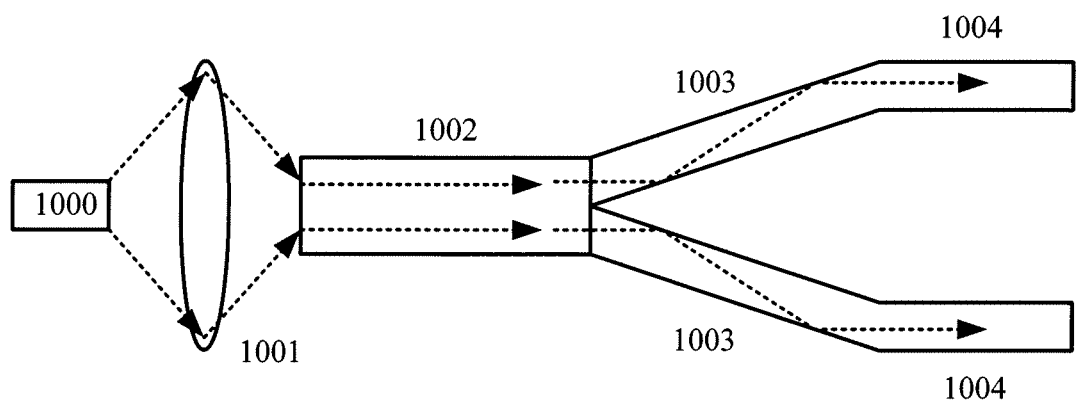
FIGS. 10, 11, and 12 illustrate exemplary light pipe configurations than can be used with a modular array including a plurality of TDI sensor modules.
Figure 11:
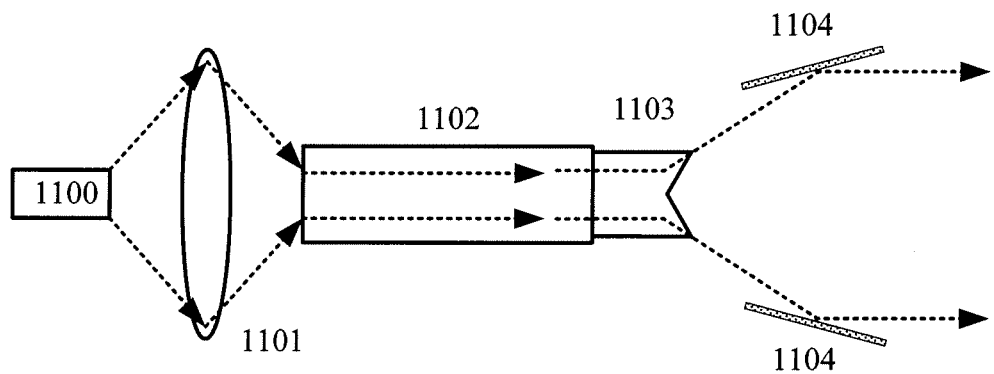
Figure 12:
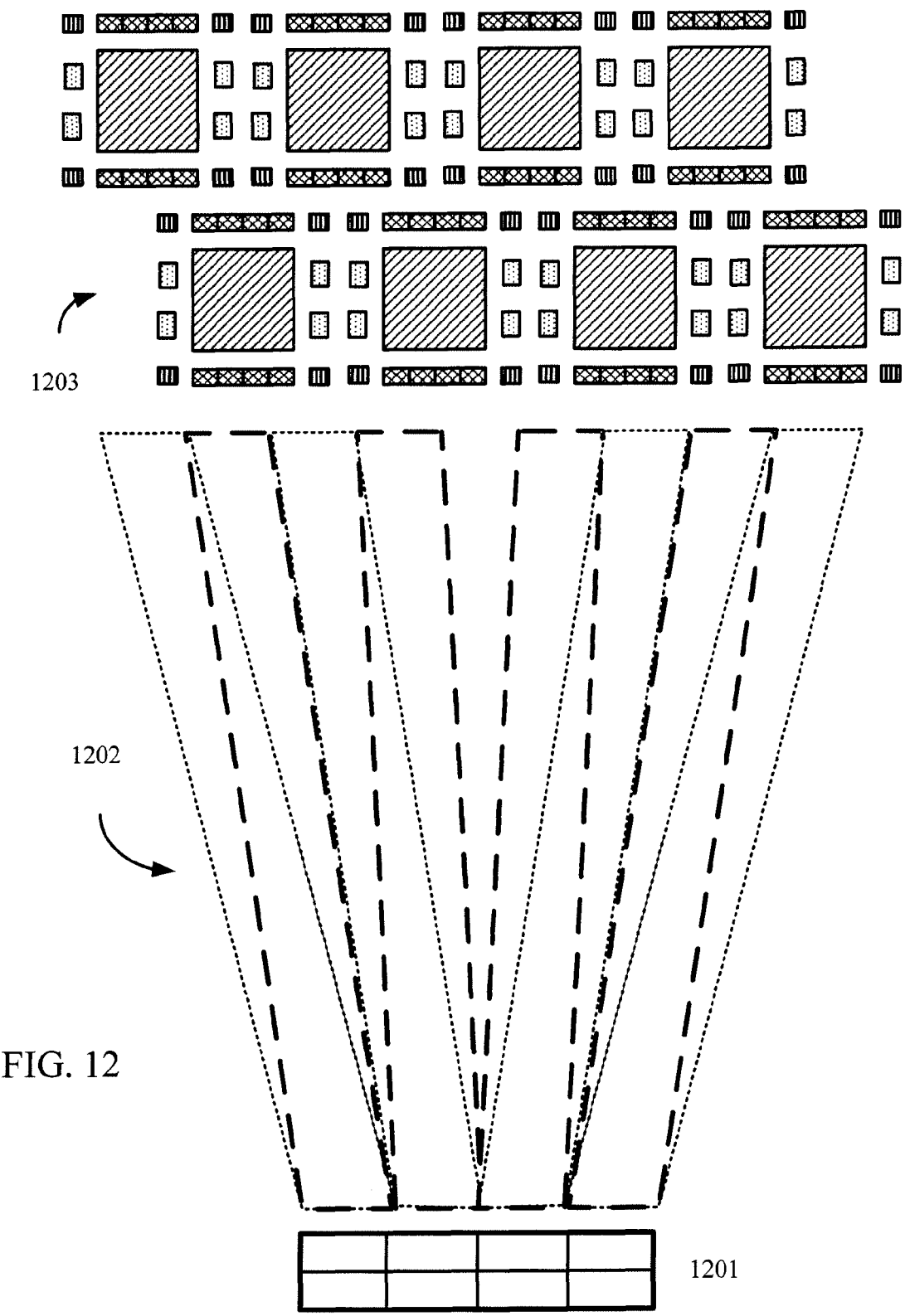

An additional advantage of using modular arrays can be found with low-brightness illumination. FIGS. 10, 11, and 12 illustrate exemplary optical homogenizer, or "light pipe" configurations that can be used with the modular arrays discussed above. In these configurations, a low-brightness source illumination can be efficiently distributed to a plurality of TDI sensor modules. For example, the light pipe configuration of FIG. 10 includes a light source 1000, a collector 1001 that collects the light from light source 1000 and redirects the light to a main light pipe 1002. A plurality of turning light pipes 1003 (two shown) direct equal portions of the light from main light pipe 1002 into associated distribution light pipes 1004. The light from distribution light pipes 1004 can be used to illuminate two TDI sensor modules of a modular array (not shown for simplicity).

In another embodiment shown in FIG. 11, the light pipe configuration includes a light source 1100, a collector 1101 that collects the light from light source 1100 and redirects the light to a main light pipe 1102. A plurality of prisms 1103 and mirrors 1104 (two shown) can direct equal portions of the light from main light pipe 1102 to illuminate two TDI sensor modules of a modular array (not shown for simplicity). An advantage of these two-stage configurations is that a non-uniform light source can be used for illumination, and the homogenizer (i.e. main light pipe 1002/1102) allows some scrambling of the light that results in a substantially uniform, equal light being provided downstream.

These light pipes can be constructed using any suitable materials for the wavelengths of interest. For example, fused silica solid glass light pipes can be used for DUV illumination. Hollow reflective-type light pipes can be used for EUV illumination. Note that grazing-incidence reflection optics can be used for DUV or EUV illumination to improve light distribution uniformity.

Note that different light pipe configurations can be used for the specific modular array embodiment, i.e. the number of TDI sensor modules that are to be illuminated. For example, FIG. 12 illustrates a light pipe configuration including a single aperture 1201 (shown as an end view for clarity) to receive light and a plurality of light pipes 1202 (eight light pipes shown) for directing the light to a TDI modular array 1203. In this embodiment, light pipes 1202 are stacked in pairs, wherein each light pipe is aligned with a specific column of TDI sensors of modular array 1203 (in this configuration, eight columns) Specifically, the light pipes 1202 represented using dotted lines are aligned with columns associated with the top row of the TDI sensors in TDI modular array 1203, whereas the light pipes represented using dashed lines are aligned with columns associated with the bottom row of the TDI sensors in TDI modular array 1203.

Figure 13:
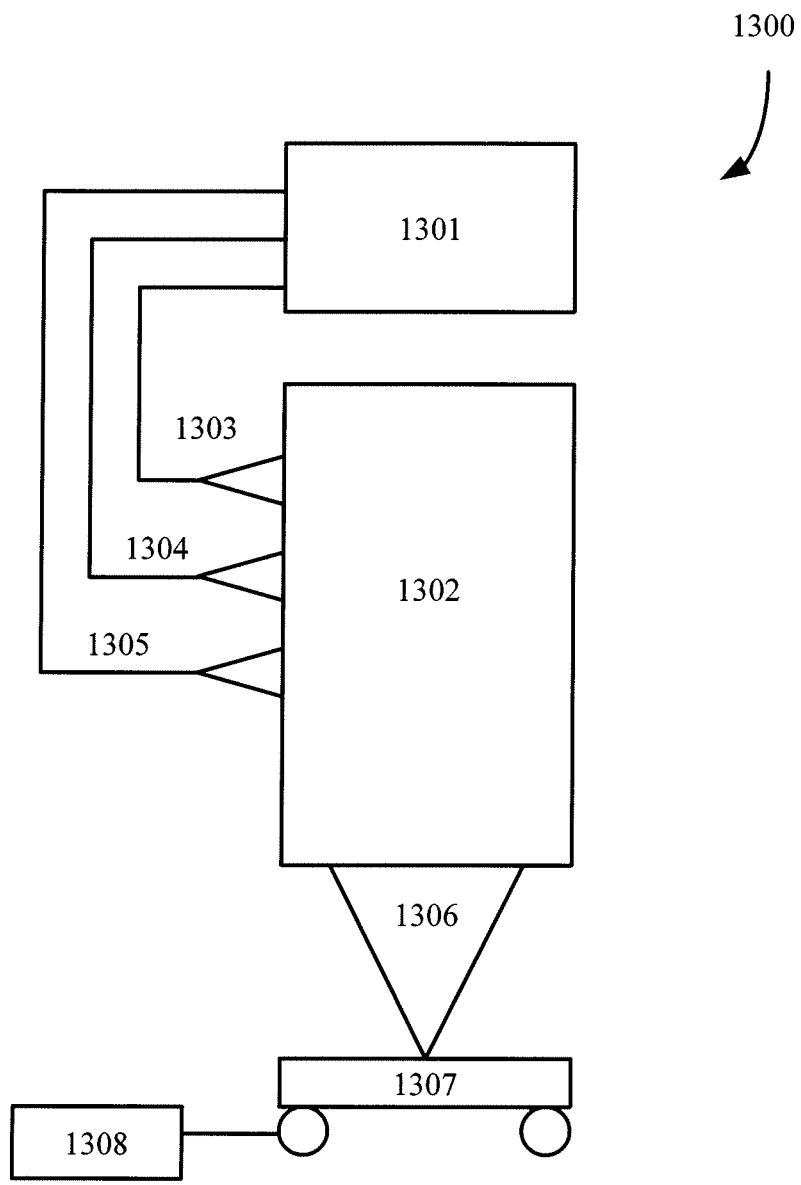
FIG. 13 depicts a simplified inspection system that can be used with the above-described modular array.

FIG. 13 depicts a simplified inspection system 1300 that can be used with the above-described modular array. An inspection surface 1307 is illuminated by any of the light pipe embodiments discussed above in reference to FIGS. 10-12. Inspection system 1300 also typically includes scanning apparatus 1308 that permits any desired portion of surface 1307 to be illuminated and inspected. Such scanning and illumination apparatus and methodologies are known to persons having ordinary skill in the art. Light 1306 from surface 1307 (reflected, scattered, diffracted, etc.) is received by an optical system 1302. Optical system 1302 is configured to receive light from surface 1307 and direct portions of the light onto a plurality of TDI sensor modules 1303, 1304, and 1305 arranged in one of the above-discussed configurations. Typically, optical system 1302 includes a plurality of optical elements (e.g., objective lens systems, beam splitters, and other optical elements) arranged so that each of TDI sensor modules 1303, 1304, and 1305 can form a composite image of surface 1307. These images are transmitted as electronic or optical data signals to an image processor 1301 capable of a wide range of signal and image processing operations. In particular, image processor 1301 can be capable of image storage, image processing and reconstruction, as well as locating, quantifying, and categorizing defects located in the surface 1307.

Note that the modular array described above can provide enhanced anti-aliasing capability similar to that provided by U.S. Pat. No. 7,227,984 (described above). Notably, the sensor arrays in Cavan have a sub-pixel shift (i.e. less than one pixel) in both the horizontal and vertical directions to achieve anti-aliasing. In contrast, a modular array can have pixel shifts in one direction significantly greater than one (e.g. two or more TDI sensor spacings (on the order of thousands of pixels) and a sub-pixel shift in another direction. In this configuration, the pixels of a modular array can be advantageously designed as standard square or rectangular elements, which improves yields and thus reduces manufacturing costs.

Although illustrative embodiments have been described in detail herein with reference to the accompanying figures, it is to be understood that the invention is not limited to those precise embodiments. They are not intended to be exhaustive or to limit the invention to the precise forms disclosed. As such, many modifications and variations will be apparent to practitioners skilled in this art. For example, to provide accurate image data, the TDI sensor modules can be physically aligned to within, for example, one pixel. However, in one embodiment, if the TDI sensor modules are not aligned to this tolerance, then software at the inspection system level can provide the necessary digital alignment.

Note that, referring back to FIG. 2B, the analog signal from the sensor can be digitized by the localized processing circuits and then can be transferred (via the transceivers 207 and optical fibers 206) to the system-level inspection components 208. This implementation (i.e. short signal path and high-speed transmission components) ensures minimal signal delay from the sensor to system-level inspection components 208.

Figure 14:
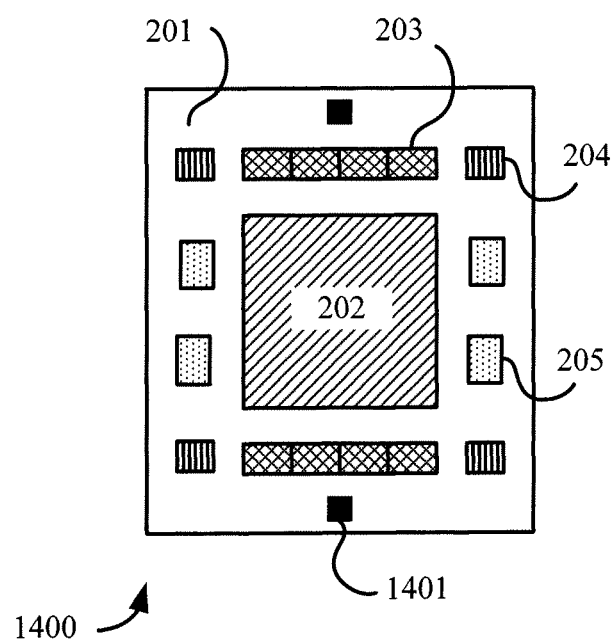
FIG. 14 illustrates another exemplary TDI sensor module, which includes an FPGA.

Note further that, referring to another TDI sensor module 1400 shown in FIG. 14, processing circuits 203 (see FIG. 2A, which explains these circuits in detail) could be supplemented by field programmable gate arrays (FPGAs) 1401, which in turn could be connected to data transceivers (see, for example, data transceivers 207 of FIG. 2B) via PCB 201. FPGAs 1401 can provide additional processing of the digitized signals from processing circuits 203. In another embodiment, processing circuits 203 can be implemented by mixed signal FPGAs.

Figure 15:
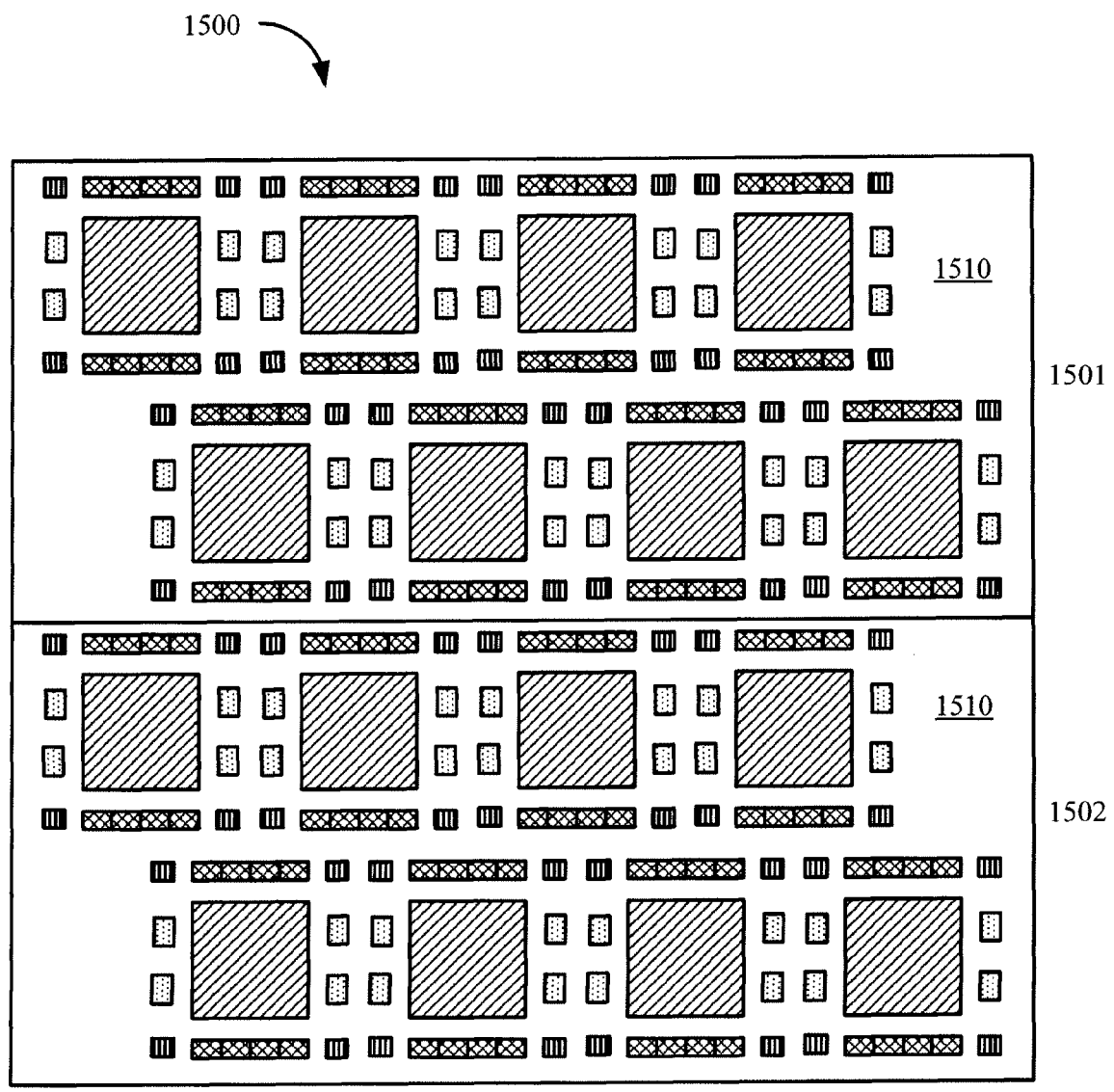
FIG. 15 illustrates a TDI modular array in which each set of TDI sensor modules is mounted on a silicon substrate.

In one embodiment, shown in FIG. 15, a TDI modular array 1500 can include sets of TDI sensor modules, each set being mounted on a silicon substrate. For example, FIG. 15 illustrates sets 1501 and 1502 of TDI sensor modules. Each set can be mounted on its own silicon substrate 1510. In another embodiment, all TDI sensor modules of a TDI modular array can be mounted on a single silicon substrate. Note that a silicon substrate can include wiring/interconnect (not shown for simplicity) for connecting each TDI sensor to its localized circuits as well as for connecting those localized circuits to data transceivers mounted on the back of the silicon substrate. In one embodiment, the silicon substrate can be implemented by cutting a wafer to the appropriate size/shape.

Notably, mounting the TDI sensor modules on a silicon substrate provides distinct advantages because the silicon substrate will expand/contract similarly to the components of the TDI sensor module, i.e. the TDI sensor modules and the silicon substrate have substantially the same thermal coefficient of expansion. Additionally, the thermal conductivity of silicon is high, thereby allowing any heating from the TDI sensor modules to be efficiently diffused by the silicon substrate.

Note that additional components, e.g. transistors, capacitors, resistors, etc., can be included in layers formed on the silicon substrate. Therefore, some processing may be performed by such components in conjunction with the processing performed by the localized circuits. Note further that the design rules for a silicon substrate (e.g. a wafer) are submicron with very small alignment errors. In contrast, a PCB has much larger design rules and alignment errors. Therefore, providing sub-pixel offsets can be ensured more easily on a silicon substrate rather than on a PCB.

Figure 16:
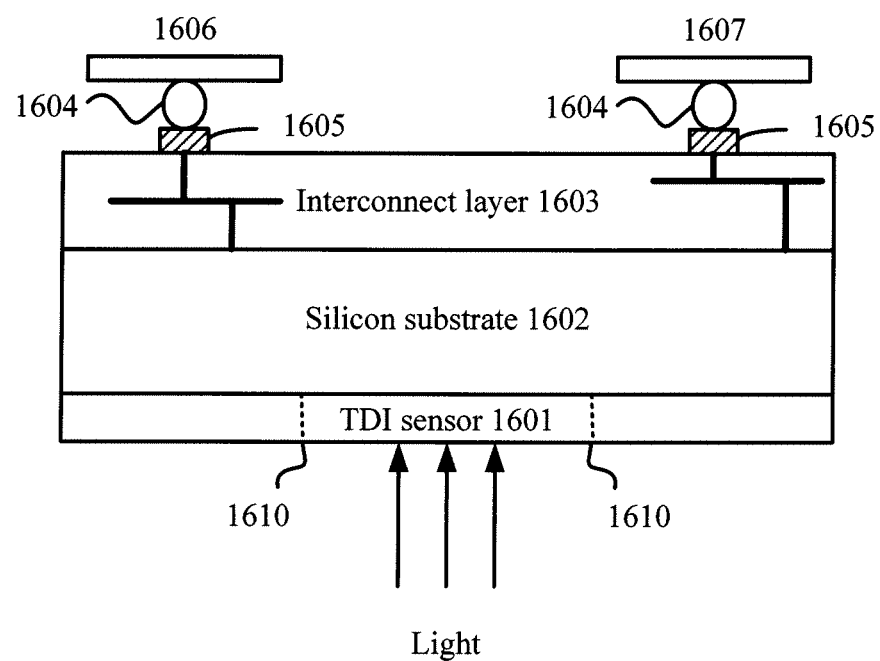
FIG. 16 illustrates another exemplary configuration of a TDI sensor module.

In another embodiment of a TDI sensor module shown in FIG. 16, a TDI sensor 1601 can be formed on one side of a silicon substrate 1602. To minimize the footprint of the TDI sensor module, TDI sensor 1601 can be formed to take up substantially all the surface area of silicon substrate 1602. An interconnect layer 1603 can be formed on the opposite of silicon substrate 1602 from TDI sensor 1601. In one embodiment, interconnect layer 1603 can include metal lines formed in oxide. The metal lines of interconnect layer 1603 can be connected to pads 1605. Note that TDI sensor 1601 and substrate 1602 also include some limited interconnect, and TDI sensor 1601 may further include some circuits for detecting the light. In this embodiment, localized circuits 1606 (one shown)(for processing and driving) and a transceiver 1607 can be packaged in ball grid arrays (BGAs), wherein the solder balls 1604 of the BGAs can be connected (and soldered) to pads 1605. In other embodiments, localized circuits 1606 and transceiver 1607 can be mounted on interconnect layer 1603 using other types of packaging. In another embodiment, the optical portion of TDI sensor 1601 can extend to borders 1610, and localized circuits 1606, transceiver 1607, and the metal lines of interconnect layer 1603 can be mounted outside border 1610.

Accordingly, it is intended that the scope of the invention be defined by the following Claims and their equivalents.

The invention claimed is:

1. An inspection system for inspecting a surface, the inspection system comprising:
   a modular array including a plurality of time delay integration (TDI) sensor modules, each TDI sensor module including:
      a TDI sensor; and
      a plurality of localized circuits for driving and processing the TDI sensor;
   an optical system configured to receive light from the surface and direct portions of the light onto the plurality of TDI sensor modules;
   an image processor for receiving data from the modular array; and
   at least one light pipe to distribute a low-brightness source illumination to the plurality of TDI sensor modules.

2. The inspection system of claim 1, further including a prism to segment and distribute light from the at least one light pipe to the plurality of TDI sensor modules.

3. The inspection system of claim 1, further including mirrors to segment and distribute light from the at least one light pipe to the plurality of TDI sensor modules.

4. The inspection system of claim 1, further including a plurality of light pipes to equally distribute light from the at least one light pipe to the plurality of TDI sensor modules.

5. An inspection system for inspecting a surface, the inspection system comprising:
   a modular array including a plurality of time delay integration (TDI) sensor modules, each TDI sensor module including:
      a TDI sensor; and
      a plurality of localized circuits for driving and processing the TDI sensor;
   an optical system configured to receive light from the surface and direct portions of the light onto the plurality of TDI sensor modules; and
   an image processor for receiving data from the modular array; wherein a first row of TDI sensor modules is offset with respect to a second row of TDI sensor modules.

6. The inspection system of claim 5, wherein the offset is lateral to a TDI scan direction.

7. The inspection system of claim 5, wherein the offset is in a TDI scan direction.

8. The inspection system of claim 5, wherein at least one of the plurality of localized circuits control a clock associated with the TDI sensor to reduce aliasing effects.

9. The inspection system of claim 1, wherein the plurality of TDI sensor modules are identical.

10. The inspection system of claim 1, wherein the plurality of TDI sensor modules include at least two TDI sensors having different integration stages.

11. The inspection system of claim 1, wherein the plurality of TDI sensor modules are aligned in a TDI scan direction.

12. The inspection system of claim 1, wherein the plurality of TDI sensor modules capture a same inspection region.

13. The inspection system of claim 5, wherein a first set of the plurality of TDI sensor modules are aligned in a TDI scan direction, a second set of the plurality of TDI sensor modules are aligned in the TDI scan direction, and the first and second sets of TDI sensor modules capture different inspection regions.

14. The inspection system of claim 5, wherein the modular array further includes a printed circuit board (PCB) for mounting and coupling the TDI sensor and the plurality of localized circuits.

15. The inspection system of claim 14, wherein the modular array further includes a data transceiver mounted on the PCB on an opposite side from the TDI sensor and the plurality of localized circuits, wherein at least one processing circuit of the plurality of localized circuits is coupled to the data transceiver.

16. The inspection system of claim 15, wherein the at least one processing circuit is a field programmable gate array (FPGA).

17. The inspection system of claim 14, wherein the modular array further includes a field programmable gate array (FPGA) that receives digitized signals from at least one of the plurality of localized circuits, the FPGA being mounted on the PCB.

18. The inspection system of claim 17, wherein the modular array further includes a data transceiver mounted on the PCB on an opposite side from the TDI sensor; the plurality of localized circuits, and the FPGA, wherein the FPGA is coupled to the data transceiver.

19. The inspection system of claim 5, wherein the modular array further includes a silicon substrate for mounting and coupling the TDI sensor and the plurality of localized circuits.

20. The inspection system of claim 19, wherein the TDI sensor and the plurality of localized circuits are formed/mounted on opposite sides of the silicon substrate.

21. The inspection system of claim 19, wherein the modular array further includes a data transceiver mounted on the silicon substrate on an opposite side from the TDI sensor and the plurality of localized circuits, wherein at least one processing circuit of the plurality of localized circuits is coupled to the data transceiver.

22. The inspection system of claim 19, wherein the modular array further includes a data transceiver, wherein the data transceiver and the plurality of localized circuits are mounted on the silicon substrate on an opposite side from the TDI sensor, wherein at least one processing circuit of the plurality of localized circuits is coupled to the data transceiver.

23. The inspection system of claim 21, wherein the at least one processing circuit is a field programmable gate array (FPGA).

24. The inspection system of claim 19, wherein the modular array further includes a field programmable gate array (FPGA) that receives digitized signals from at least one of the plurality of localized circuits, the FPGA being mounted on the silicon substrate.

25. The inspection system of claim 24, wherein the modular array further includes a data transceiver mounted on the silicon substrate on an opposite side from the TDI sensor, the plurality of localized circuits, and the FPGA, wherein the FPGA is coupled to the data transceiver.

26. A modular array for an inspection system, the modular array comprising:
a plurality of time delay integration (TDI) sensor modules, each TDI sensor module including:
a TDI sensor; and
a plurality of localized circuits for driving and processing the TDI sensor,
wherein a first row of TDI sensor modules is offset with respect to a second row of TDI sensor modules.

27. The modular array of claim 26, wherein the offset is lateral to a TDI scan direction.

28. The modular array of claim 26, wherein the offset is in a TDI scan direction.

29. The modular array of claim 26, wherein at least one of the plurality of localized circuits control a clock associated with the TDI sensor to reduce aliasing effects.

30. The modular array of claim 26 wherein the plurality of TDI sensor modules are identical.

31. The modular array of claim 26, wherein the plurality of TDI sensor modules include at least two TDI sensors having different integration stages.

32. The modular array of claim 26, wherein the plurality of TDI sensor modules are aligned in a TDI scan direction.

33. The modular array of claim 26, wherein the plurality of TDI sensor modules capture a same inspection region.

34. The modular array of claim 26, wherein a first set of the plurality of TDI sensor modules are aligned in a TDI scan direction, a second set of the plurality of TDI sensor modules are aligned in the TDI scan direction, and the first and second sets of TDI sensor modules capture different inspection regions.

35. The modular array of claim 26, further including a printed circuit board (PCB) for mounting and coupling the TDI sensor and the plurality of localized circuits.

36. The modular array of claim 35, further including a data transceiver mounted on the PCB on an opposite side from the TDI sensor and the plurality of localized circuits, wherein at least one processing circuit of the plurality of localized circuits is coupled to the data transceiver.

37. The modular array of claim 36, wherein the at least one processing circuit is a field programmable gate array (FPGA).

38. The modular array of claim 35, further including a field programmable gate array (FPGA) that receives digitized signals from at least one of the plurality of localized circuits, the FPGA being mounted on the PCB.

39. The modular array of claim 38, further including a data transceiver mounted on the PCB on an opposite side from the TDI sensor, the plurality of localized circuits, and the FPGA, wherein the FPGA is coupled to the data transceiver.

40. A modular array for an inspection system, the modular array comprising:
a plurality of time delay integration (TDI) sensor modules, each TDI sensor module including:
a TDI sensor; and
a plurality of localized circuits for driving and processing the TDI sensor; and
a silicon substrate for mounting and coupling the plurality of TDI sensor modules, the plurality of TDI sensor modules and the silicon substrate having substantially a same thermal coefficient of expansion.

41. The inspection system of claim 40, wherein the TDI sensor and the plurality of localized circuits are formed/mounted on opposite sides of the silicon substrate.

42. The modular array of claim 40, further including a data transceiver mounted on the silicon substrate on an opposite side from the TDI sensor and the plurality of localized circuits, wherein at least one processing circuit of the plurality of localized circuits is coupled to the data transceiver.

43. The inspection system of claim 40, wherein the modular array further includes a data transceiver, wherein the data transceiver and the plurality of localized circuits are mounted on the silicon substrate on an opposite side from the TDI sensor, wherein at least one processing circuit of the plurality of localized circuits is coupled to the data transceiver.

44. The modular array of claim 42, wherein the at least one processing circuit is a field programmable gate array (FPGA).

45. The modular array of claim 40, further including a field programmable gate array (FPGA) that receives digitized signals from at least one of the plurality of localized circuits, the FPGA being mounted on the silicon substrate.

46. The modular array of claim 45, further including a data transceiver mounted on the silicon substrate on an opposite side from the TDI sensor, the plurality of localized circuits, and the FPGA, wherein the FPGA is coupled to the data transceiver.

* * * * *